(12) United States Patent
Tokieda et al.

(10) Patent No.: US 8,701,504 B2
(45) Date of Patent: Apr. 22, 2014

(54) AUTOMATIC ANALYZER AND SAMPLE-PROCESSING SYSTEM

(75) Inventors: Hitoshi Tokieda, Hitachinaka (JP); Yoshimitsu Takagi, Hitachinaka (JP); Masashi Akutsu, Hitachinaka (JP); Shotaro Sagawa, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 286 days.

(21) Appl. No.: 13/059,511

(22) PCT Filed: Aug. 28, 2009

(86) PCT No.: PCT/JP2009/065453
§ 371 (c)(1),
(2), (4) Date: Mar. 15, 2011

(87) PCT Pub. No.: WO2010/032628
PCT Pub. Date: Mar. 25, 2010

(65) Prior Publication Data
US 2011/0162438 A1    Jul. 7, 2011

(30) Foreign Application Priority Data
Sep. 16, 2008    (JP) .................................. 2008-235848

(51) Int. Cl.
*G01N 1/10* (2006.01)
(52) U.S. Cl.
USPC .................. 73/863.01; 73/863.31; 73/864.91; 422/67
(58) Field of Classification Search
USPC ................................ 73/863.01, 61.59; 422/67
See application file for complete search history.

(56) References Cited

U.S. PATENT DOCUMENTS

| | | | | |
|---|---|---|---|---|
| 5,439,645 A | * | 8/1995 | Saralegui et al. | 422/64 |
| 5,777,902 A | * | 7/1998 | Ono et al. | 702/22 |
| 2009/0162247 A1 | * | 6/2009 | Tokieda et al. | 422/65 |

FOREIGN PATENT DOCUMENTS

| | | | |
|---|---|---|---|
| JP | 10-019899 | * | 1/1998 |
| JP | 10-019899 A | | 1/1998 |
| JP | 10-213586 A | | 8/1998 |
| JP | 2000-088861 A | | 3/2000 |
| JP | 2000-105246 A | | 4/2000 |
| JP | 2004-28588 | * | 1/2004 |
| JP | 2004-028588 A | | 1/2004 |

OTHER PUBLICATIONS

English Translation of JP 10-019899.*
English Translation of JP 2004-28588.*

* cited by examiner

*Primary Examiner* — Hezron E Williams
*Assistant Examiner* — Alexander Mercado
(74) *Attorney, Agent, or Firm* — Mattingly & Malur, PC

(57) ABSTRACT

In a sample-processing system that includes one or more function modules and one or more buffer units each combined as a pair with one of the function modules, in case of device stoppage due to failure, since a number of sample racks are held in the buffers, resetting involves a huge amount of time for storage of the racks. In addition, if the system configuration includes a plurality of buffer units, the resetting time increases with the number of buffer units. Sample rack ID reading means is provided in each buffer unit and during resetting, IDs of the sample racks in the buffer unit are read in the buffer unit. The buffer unit then uses the read information to make an inquiry to a control unit as to transport destinations of each sample rack. After this, sample processing based on transport destination instructions from the control unit is restarted using the buffer unit as a restarting position.

5 Claims, 15 Drawing Sheets

AUTOMATIC ANALYZER AND SAMPLE-PROCESSING SYSTEM

TECHNICAL FIELD

The present invention relates generally to automatic analyzers that conduct qualitative and quantitative analyses upon biological samples of blood, urine, and the like, and to sample-processing systems used for processes that include analysis in addition to pre-processing such as centrifugal separation. More particularly, the invention relates to an automatic analyzer and sample-processing system suitable for achieving efficient operation of multiple devices each different in processing capabilities as well as in functionality, each device being interconnected along a transport line for transporting sample racks.

BACKGROUND ART

Analytical results on biological samples of blood plasma, serum, urine, and the like, provide a great deal of information useful for diagnosing disease. A large number of conventional techniques exist that relate to the apparatuses that automatically process such biological samples.

Patent Document 1, for example, discloses a technique in which an automatic analyzer includes a plurality of independent transfer means, one for loading racks into analyzing units and the other for unloading the racks from the analyzing units, further includes, upstream relative to the analyzing unit, means for identifying requested analytical items on a sample-by-sample basis. In this conventional technique, the analyzer determines which of the multiple analyzing units is to be used to execute the analysis relating to a requested item, and gives an instruction for loading one of the racks into a corresponding analytical module.

In addition, Patent Document 2 discloses an automatic analyzer that includes a plurality of analyzing units arranged along a transport line inclusive of a conveyor belt, with a rack supply unit disposed at one end of the transport line and a rack recovery unit at the other end thereof. The analyzer further includes a rack standby unit in front of the rack recovery unit so as to enable automatic re-inspection.

PRIOR ART REFERENCES

Patent Documents

Patent Document 1: JP-10-19899-A
Patent Document 2: JP-10-213586-A

SUMMARY OF THE INVENTION

Problems to be Solved by the Invention

In the automatic analyzer described in Patent Document 1, a transport route of racks is determined before the racks are transported to an analyzing unit. If a plurality of analyzing units are required for assay, therefore, the racks are transported in order from the upstream side. This means that when there are a number of samples to be analyzed at the upstream side, the rack transport route becomes congested and any samples that require only analysis at the downstream side are not transportable to the respective destinations earlier than the samples requiring the analysis at the upstream side.

Additionally, in the automatic analyzer described in Patent Document 2, although a return route for rack transport from the downstream side to the upstream side is provided, even if a rack is transported to an analyzing unit located at the downstream side first, this requires returning the particular rack to the rack supply unit present at the upstream end and then transporting the rack to an analyzing unit present at the upstream side. This transport sequence is not only time-consuming; it also obstructs the processing of a rack supplied from the supply unit.

Furthermore, since samples that require automatic re-inspection are collectively placed in the standby unit located in front of a rack storage unit, even if, in a system configuration with a plurality of analyzing units each different in processing rate, there are racks waiting for re-inspection after output of their processing results, these racks are unable to pass the racks earlier collected into the standby unit. That is, a wasteful waiting time occurs. For re-inspection, therefore, the above problems also occur. That is, since the samples that have been collectively placed in the standby unit also need to be later returned to the rack supply unit, this operation is time-consuming, obstructing a traveling route of the racks supplied.

The present invention is intended to provide, as a solution to these problems, a system configuration with buffer units each paired with a function module. In case of analyzer stoppage due to some kind of trouble or failure, however, the apparatus needs resetting to enable a plurality of sample racks to be stored into each buffer unit, and the resetting process itself can cause a problem.

When resetting is executed, sample vessel identification code reading or sample rack identification code reading usually needs to be repeated once again before processing can be restarted. This processing sequence prevents an operator from mistaking the sample for a sample not to undergo processing. If the processing sequence is not observed, the positions of the racks being carried, for example, become indeterminate or whether the sample is the correct one to undergo processing is unverifiable if the sample racks in the analyzer are removed manually by the operator during the stoppage of the analyzer.

In other words, it is necessary, after resetting, to return all sample racks to the storage unit and for the operator to reload the racks, with the result that a huge amount of resetting time is required particularly in a system having buffer units and processing a large quantity of racks, as in one configuration achieved by the present invention.

In order to alleviate this problem, for example the system described in Japanese Patent No. 3655509 includes means for reading a sample vessel identification code or sample rack identification code with a reading unit on a sample rack transport route and using the read information to define a transport route (branch) before processing the sample.

However, since the sample racks unconditionally need to be carried to the reading unit in order, congestion occurs on the transport route to the reading unit, thus reducing efficiency particularly in a system configuration including a plurality of modules. The above also causes a problem such as the inconvenience that a sample to undergo urgent processing cannot be carried forward for processing earlier than that of other samples.

An object of the present invention is to provide an automatic analyzer and sample-processing system suitable for achieving efficient operation of multiple devices each different in processing capabilities as well as in functionality, each device being interconnected along a transport line for transporting sample racks.

Means for Solving the Problems

System and apparatus configurations according to the present invention, intended to achieve the above object, are as follows:

An automatic analyzer according to an aspect of the invention includes: a sample-processing device that processes samples; a sample buffer paired with the sample-processing device, the sample buffer supplying each of the samples to the sample-processing device; and a sample transport device that transports each sample to the sample buffer, wherein the sample buffer includes means that reads identification information on the sample.

In a sample-processing system according to another aspect of the invention, one or more function modules having a different function and processing capabilities of a device such as an analyzer or pre-processing device, and buffer units each combined as a pair with one of the function modules are interconnected via a sample rack transport section that holds a sample vessel and includes a loading unit, transport unit, and storage unit for sample racks each having a specific identification code, wherein each of the buffer units undertakes both bi-directional transfer of the sample racks to and from the sample rack transport section and transport of the sample racks to and from each function module paired with one of the buffer units, each buffer unit including: independent slots that each act as a buffer capable of holding a plurality of sample racks; a sample rack mover that is capable of loading and unloading the sample racks into and from any one of the slots; and means that reads the identification codes assigned to each of the sample racks, and wherein, upon the system being reset, the buffer unit reads the identification code of each sample rack within the buffer unit, then determines a transport destination of the sample rack from the read information and an operational state of the function module, and restarts processing.

Effects of the Invention

In the present invention, since the sample rack identification code reading means is provided in each buffer unit, the sample rack information in the buffer unit is clearly defined therein, which prevents a plurality of sample racks from being positioned at one place on the rack transport unit and leads to significant reduction in time from resetting to the restart of processing.

In addition, since all sample racks in the buffer unit are temporarily stored into the buffer slots, processing can be restarted with priority given to samples higher in a level of urgency.

Furthermore, even in a system configuration with a plurality of function modules, rapid processing independent upon the system configuration is implemented because of parallel processing via the buffer units paired with the function modules.

MODES FOR CARRYING OUT THE INVENTION

System configurations, and transfer of sample racks, in the present invention are first described below.

Figure 1:
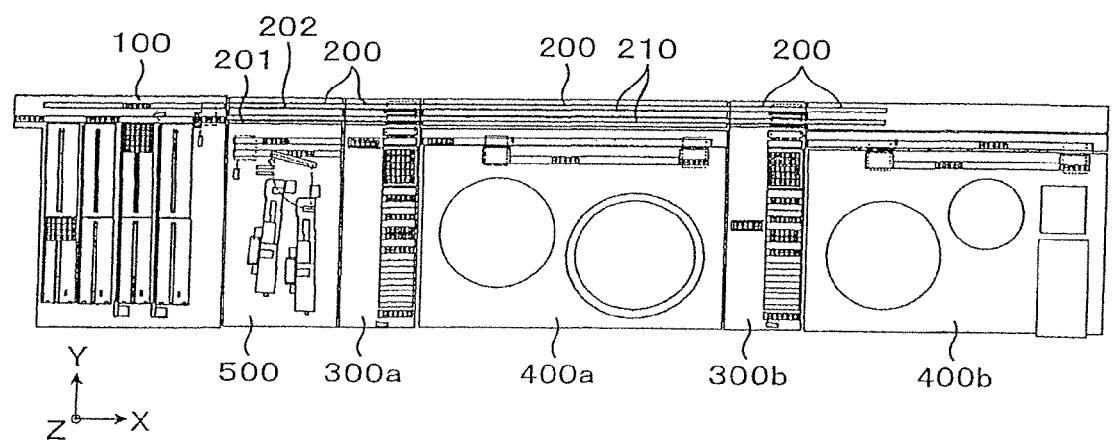
FIG. 1 is a plan view that shows a sample-processing system configuration in one embodiment of the present invention.

FIG. 1 is a plan view of a sample-processing system according to one embodiment of the present invention. The system shown by way of example in FIG. 1 includes: a sampler unit 100 that loads and unloads sample racks into and from the system; a rack transport unit 200 that transports each sample rack between the sampler unit and each of function modules; buffer units 300*a* and 300*b* arranged along the rack transport unit 200 to transfer the sample rack to and from the rack transport unit 200 and to temporarily make the sample rack stand by inside; the function modules 400*a* and 400*b* that form pairs with the buffer units 300*a*, 300*b*, and are arranged to the right thereof; and an ancillary module 500 disposed to the left of the buffer unit 300*a*.

Figure 2:
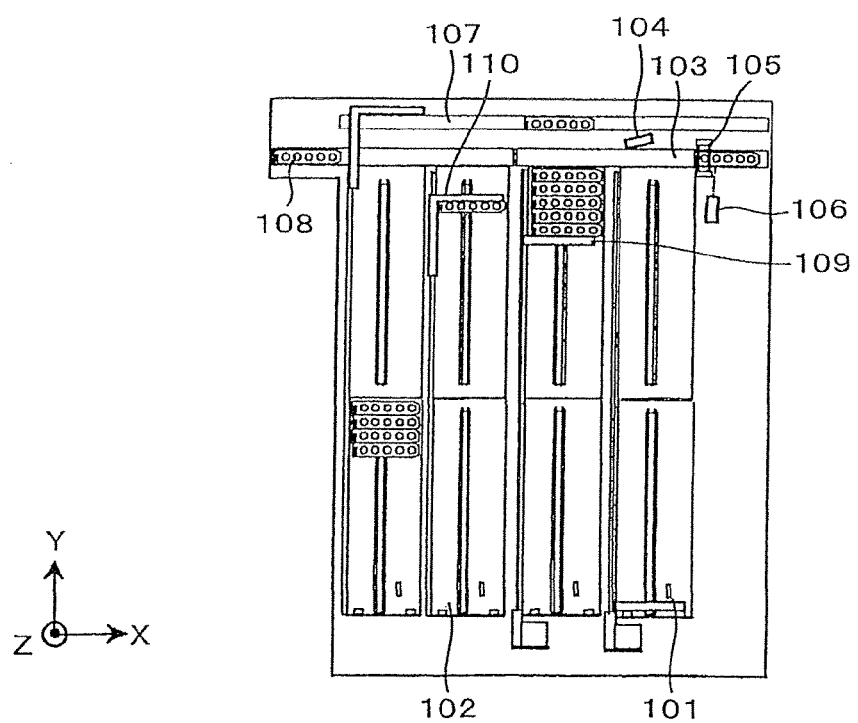
FIG. 2 is a plan view that shows a sampler unit configuration in the one embodiment of the present invention.

FIG. 2 shows a configuration of the sampler unit 100.

The sampler unit 100 includes: a loader 101 for loading the sample rack into the system; an unloader 102 for unloading the sample rack from the system; a load rack moving unit 103 for moving the sample rack from the loader to the rack transport unit 200; a rack ID reading unit 104 for reading an ID of the sample rack; a sample vessel height detection unit 105 for confirming whether sample vessels are set up on the sample rack, as well as for detecting height of each sample vessel; a sample ID reading unit 106 for reading the sample ID affixed to the sample vessel set up on the sample rack; an unload rack moving unit 107 for moving the rack from the rack transport unit 200 to the unloader 102; and an urgent sample loader 108 for loading into the sample-processing system either an urgent sample rack or a sample rack carried in from a sample transport system connected at an upstream side relative to the sample-processing system.

The sample rack set up in the loader 101 is carried to the load rack moving unit 103 by a loading lever 109. The load rack moving unit 103, after receiving the sample rack from the loader, moves the sample rack to the rack ID reading unit 104. After the rack ID reading unit 104 has read the ID of the rack, the load rack moving unit 103 further moves the sample rack to the sample vessel height detection unit 105.

The sample vessel height detection unit 105 confirms whether sample vessels are set up at different positions on the sample rack, and detects the height of each sample vessel.

After this, the sample rack is moved to a sample ID reading position, where the sample ID reading unit 106 then reads the ID of each sample.

A necessary process for the sample rack is determined from the read rack ID and sample ID information, and a function module to which the sample rack is to be transported is determined.

After the transport destination of the sample rack has been determined, the load rack moving unit 103 moves the sample rack to the rack transport unit 200.

An urgent sample rack or a sample rack that has been carried in from the sample transport system connected at an upstream side relative to the sampler unit is loaded from the urgent sample loader 108 into the sampler unit 100. The rack loaded from the urgent sample loader 108 undergoes substantially the same process as that of the rack from the aforementioned sample loader 101, and the processed rack is moved to the rack transport unit 200.

In addition, the sample rack that has gone through the necessary process in the function module is carried to the front of the unloader 102 by the unload rack moving unit 107 and stored into the unloader 102 by an unloading lever 110.

The rack transport unit 200 in FIG. 1 has two rack transport lanes, namely, a supply lane 201 that carries the sample rack from the sampler unit 100 to the function modules 400a, 400b, and a return lane 202 that returns the sample rack from the function modules 400a, 400b to the sampler unit 100.

Figure 3:
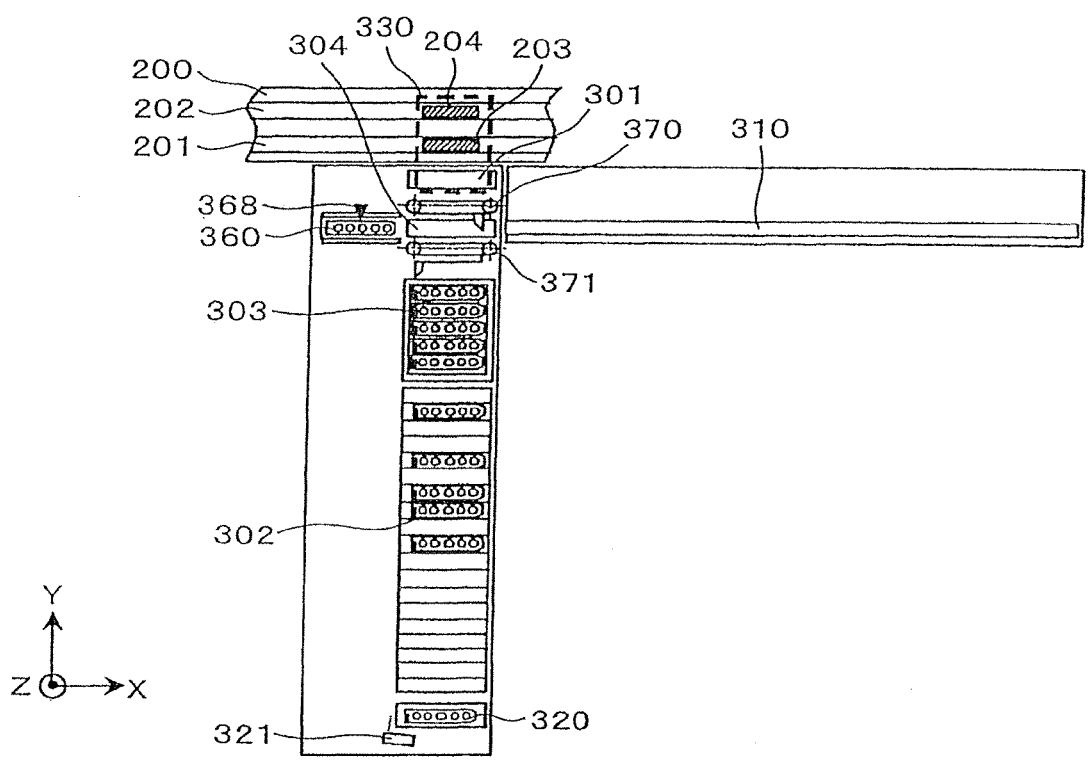
FIG. 3 is a plan view that shows a buffer unit configuration in the one embodiment of the present invention.

FIG. 3 shows a configuration of the buffer unit 300.

The buffer unit 300 includes a rack loading/unloading standby unit 301, a buffer 302, a cold storage unit 303, a module loading/unloading standby position 304, a rack transport unit 310, a one-rack loader/unloader 320, and an ID reader 321. The buffer unit 300 further includes a rack transfer mechanism 330, a rack-moving mechanism 360, and rack-unloading mechanisms 370 and 371, as drives, which move the sample rack.

The rack loading/unloading standby unit 301 has a space for making one rack stand by therein. This space acts as both a standby position for transferring the sample rack from the rack transport unit 200 to the buffer unit 300, and a standby position for accepting a sample rack to be unloaded from the buffer unit 300 onto the rack transport unit 200.

The buffer 302 includes a plurality of independent slots each formed to enable sample racks to be temporarily made to stand by therein.

The cold storage unit 303 is constructed so that a plurality of sample racks on which the samples required to undergo periodical accuracy management and/or other processing in the function modules are set up can be made to stand by in the cold storage unit 303. The cold storage unit 303 has a cold storage function to prevent evaporation of the samples.

The module loading/unloading standby position 304 has a space for making one rack stand by therein, and the space acts as a position for loading a processed sample rack from the function module into the buffer unit 300, as well as a position for unloading the sample rack from the buffer unit 300 into the function module 400.

The rack transport unit 310 carries the sample rack between the module loading/unloading standby position 304 and the function module 400.

The one-rack loader/unloader 320 loads and unloads the sample rack into and from the function module not via the rack transport unit 200, for processing in the function module.

The rack transfer mechanism 330 transfers the sample rack bi-directionally in a Y-direction between the rack loading/unloading standby unit 301 and the supply lane 201 of the rack transport unit 200 and between the rack loading/unloading standby unit 301 and the return lane 202 of the rack transport unit 200.

The sample rack that has been carried from the sampler unit 100 to the supply lane 201 moves to the rack loading/unloading position on the supply lane that is the position from which the rack is to be transferred to the buffer unit 300. The buffer unit 300 uses the rack transfer mechanism 330 to move the sample rack to the rack loading/unloading standby unit 301.

In addition, when the rack that has undergone processing in the buffer unit 300 is to be transported to the storage unit 102, the rack is unloaded from the rack loading/unloading standby unit 301 into a rack loading/unloading position 204 on the return lane by the rack transfer mechanism 330. After this, the return lane 202 carries the rack to the unload rack moving unit 107 of the sampler unit.

Next, how a rack moves in the buffer unit 300 is described below.

The rack-moving mechanism 360 includes a bucket 361 that holds one rack and moves in the Y-direction with the rack in the bucket, an X-mechanism 362 that moves in the Y-direction with the bucket containing the rack and moves the rack in an X-direction, and a carriage 363 connected to the X-mechanism and constructed to move vertically.

Detailed operation of the rack-moving mechanism in an example of moving a sample rack from the rack loading/unloading standby unit 301 to the buffer 302 is described below using FIGS. 4 to 7.

Figure 4:
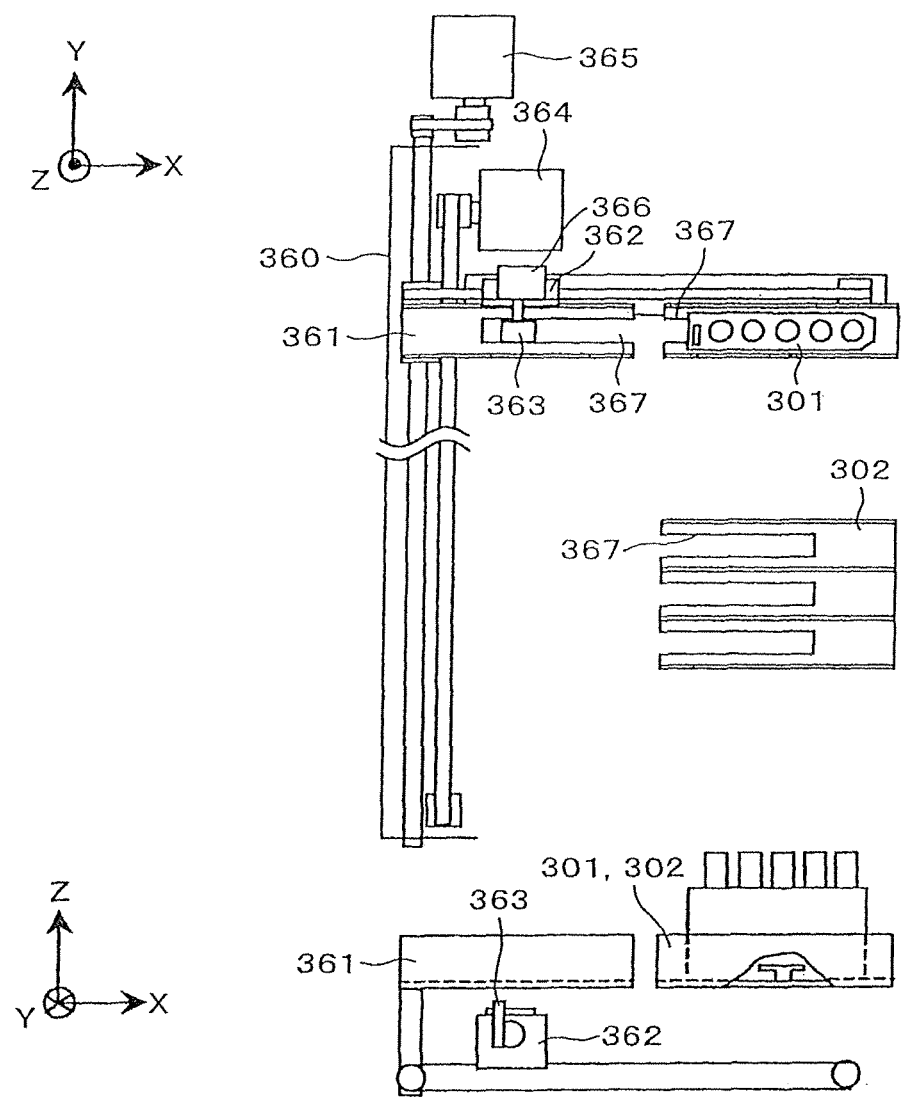
FIG. 4 is a diagram that illustrates a configuration and operation of a buffer unit rack moving mechanism.
Figure 5:
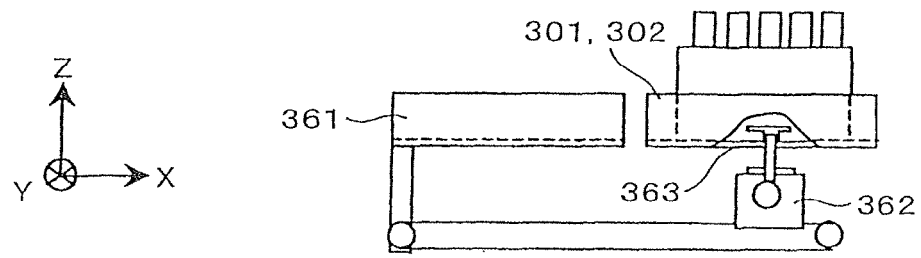
FIG. 5 is another diagram that illustrates the configuration and operation of the buffer unit rack moving mechanism.

The rack-moving mechanism 360 first drives a Y-axial driving motor 364 to move the bucket 361 to a position of the rack loading/unloading standby unit 301, as shown in FIG. 4. At the same time, the rack-moving mechanism 360 also drives an X-axial driving motor 365 to move the carriage 363 connected to the X-mechanism 362 to a position under the sample rack in the rack loading/unloading standby unit 301. Next, upon the carriage 363 being moved to a position in which it engages with a groove in the bottom of the sample rack, the rack-moving mechanism 360 drives a Z-axial driving motor 366 to move the carriage 363 upward, as shown in FIG. 5.

On sample rack transport surfaces of the bucket 361 and the rack loading/unloading standby unit 301, a slit 367 is provided to make the carriage 363 movable in the X-direction during the upward movement of the carriage. A similar slit is also provided in the buffer 302, the cold storage unit 303, and other sections that move the sample rack using the rack-moving mechanism 360.

Figure 6:
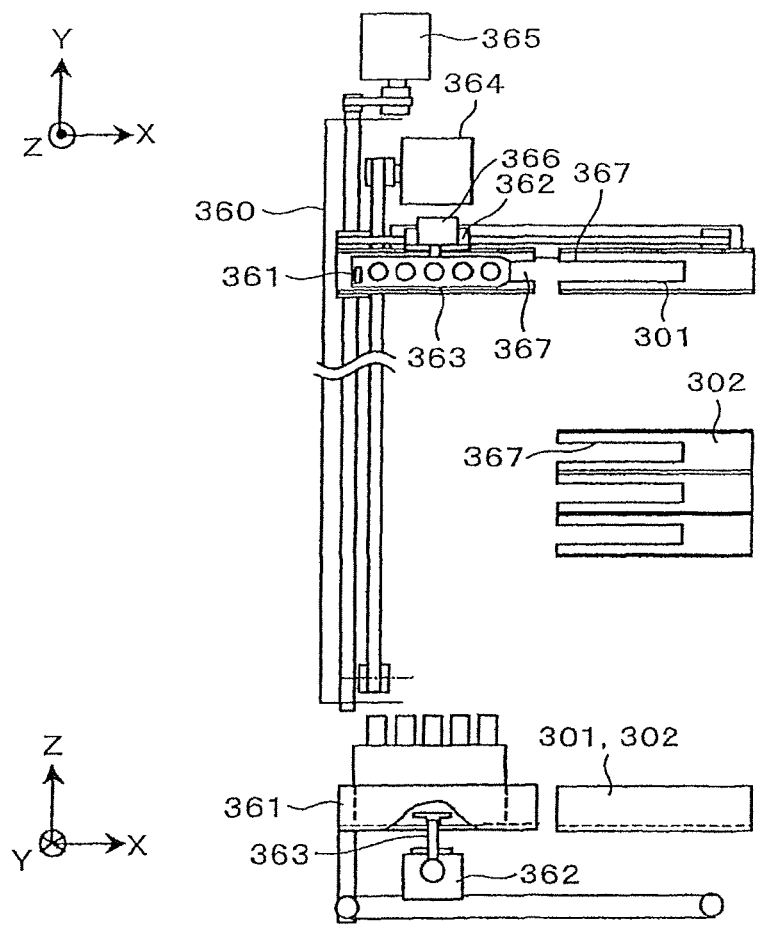
FIG. 6 is yet another diagram that illustrates the configuration and operation of the buffer unit rack moving mechanism.

Next, the rack-moving mechanism 360 drives the X-axial driving motor 365 to move the carriage 363 to a position under the bucket 361. This places the sample rack in the bucket 361, as shown in FIG. 6.

After the placement of the sample rack in the bucket 361, the rack-moving mechanism 360 drives the Y-axial driving motor 364 to move the bucket 361 to a slot position on the buffer 302. During this movement, the carriage 363 remains moved upward. This prevents the rack within the bucket from moving in the X-direction and sliding out from the bucket.

Figure 7:
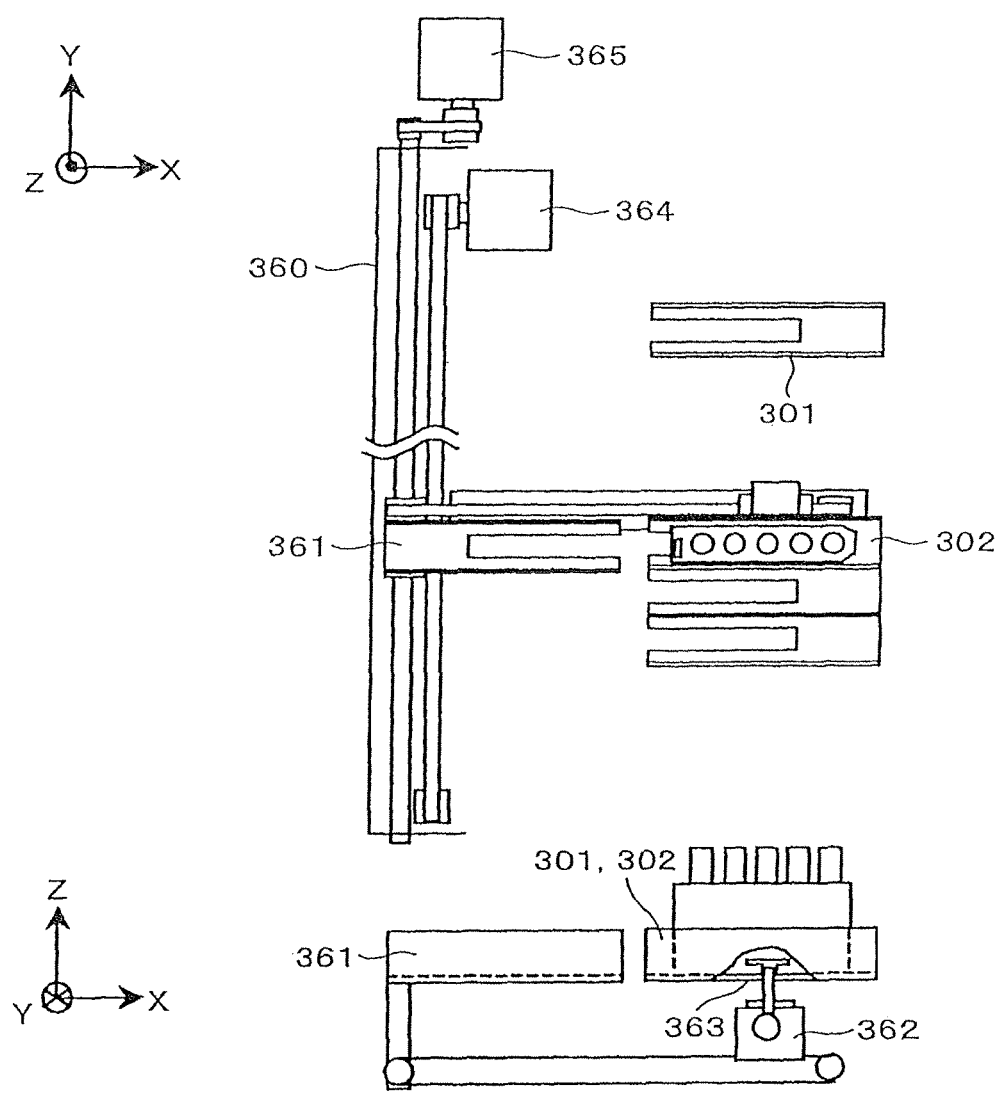
FIG. 7 is a further diagram that illustrates the configuration and operation of the buffer unit rack moving mechanism.

After the movement of the bucket to the slot position on the buffer 302, the rack-moving mechanism 360 drives the X-axial driving motor 365 to move the carriage 363 to a position under the slot and thus move the sample rack to the slot position on the buffer 302, as shown in FIG. 7.

While the movement of the rack from the rack loading/unloading standby unit 301 to the bucket 361 has been described in the present embodiment, movement of a sample rack from the buffer 302, the cold storage unit 303, or the like to the bucket 361, is also conducted in substantially the same manner as that described above. Additionally, although rack movement from the bucket 361 to the buffer 302 has been described, substantially the same manner as described above also applies to moving a sample rack to the cold storage unit 303, the module loading/unloading standby position 304, or the like. Random access to a desired sample rack is possible by providing independent sample-rack standby slots in system components such as the buffer 302.

Figure 8:
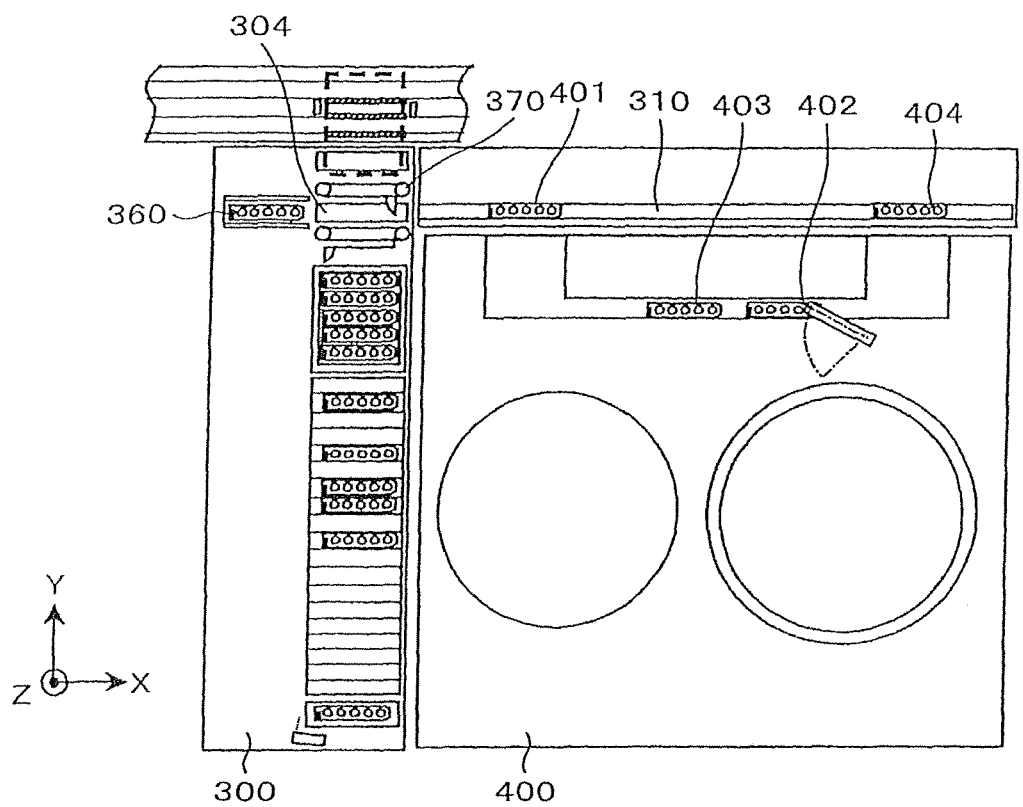
FIG. 8 is a diagram that illustrates rack transport between the buffer unit and a function module, in the one embodiment of the present invention.
Figure 9:
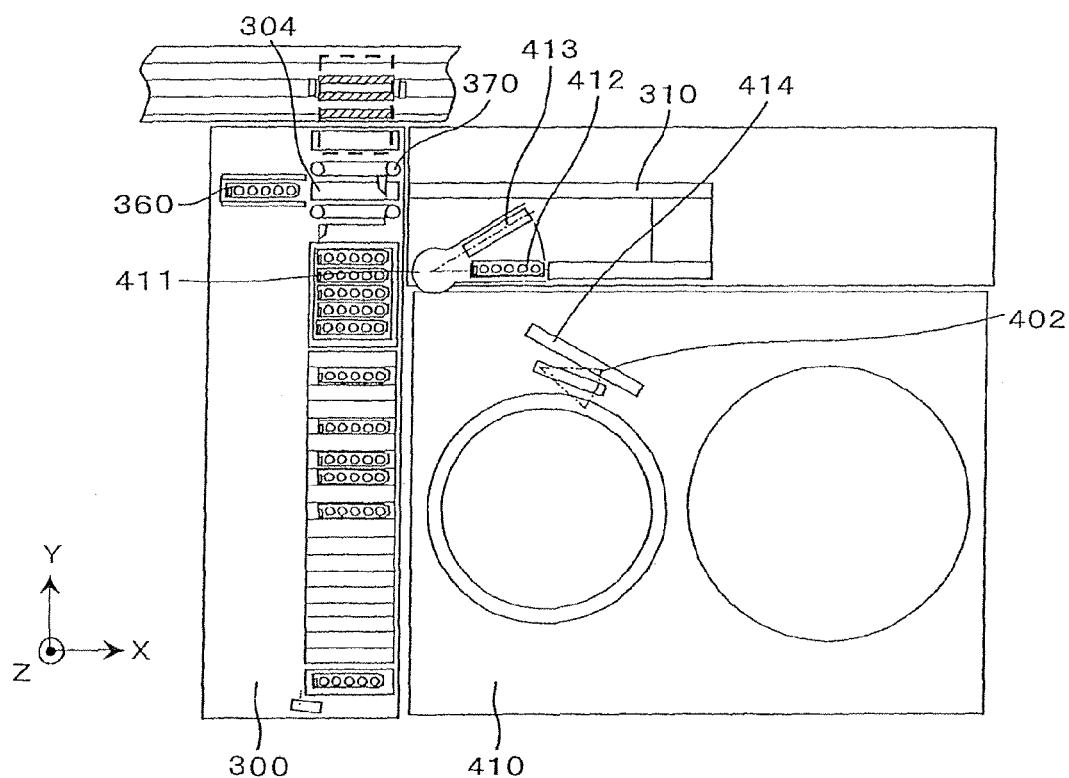
FIG. 9 is a diagram that illustrates rack transport between a buffer unit and function module in another embodiment of the present invention.
Figure 10:
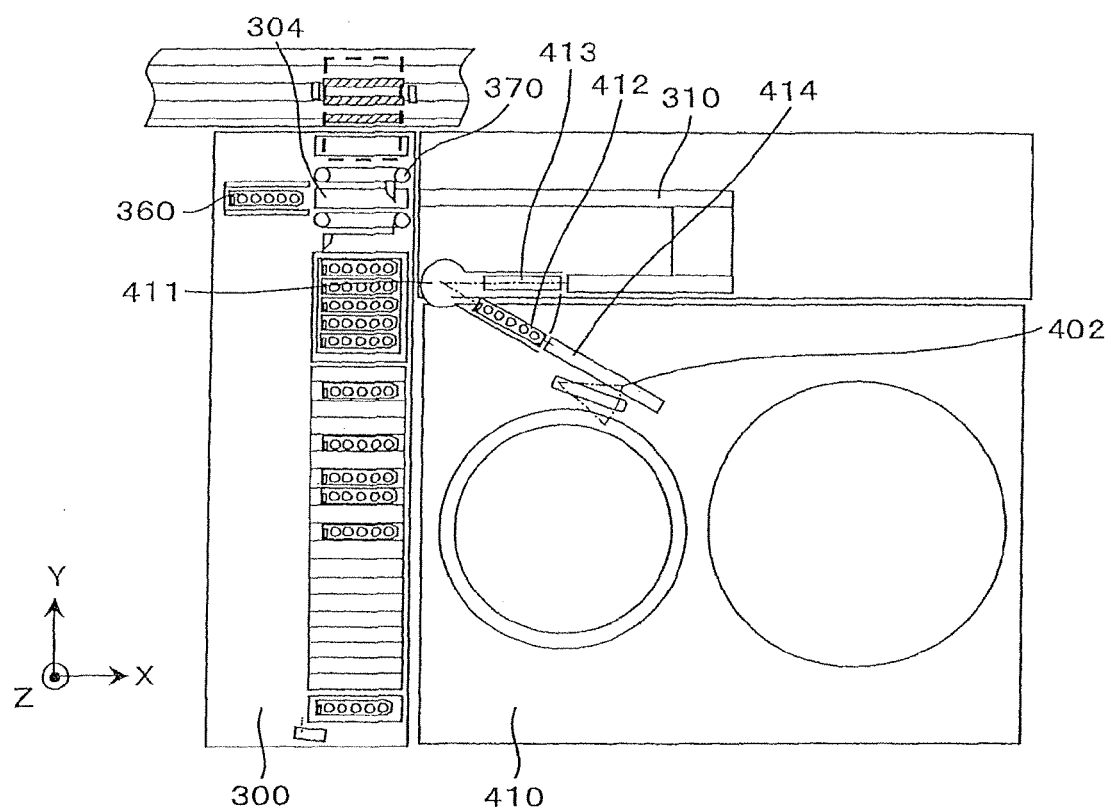
FIG. 10 is another diagram that illustrates rack transport between the buffer unit and function module in another embodiment of the present invention.
Figure 11:
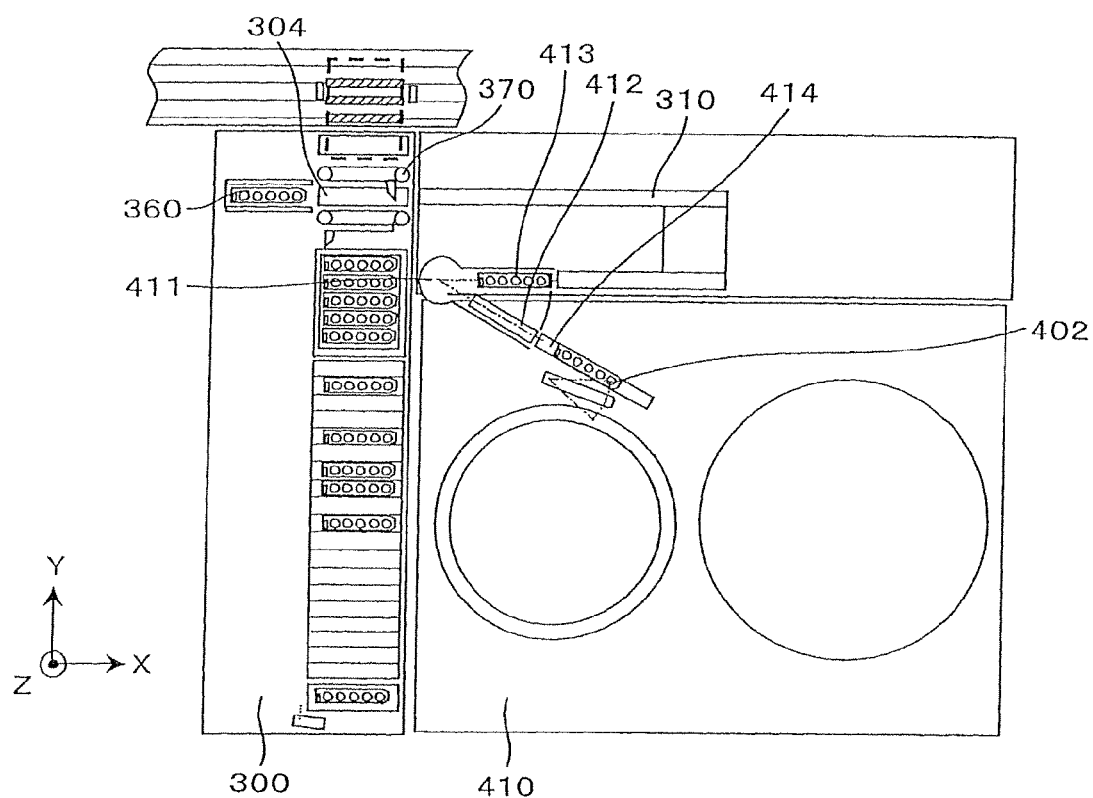
FIG. 11 is yet another diagram that illustrates rack transport between the buffer unit and function module in another embodiment of the present invention.
Figure 12:
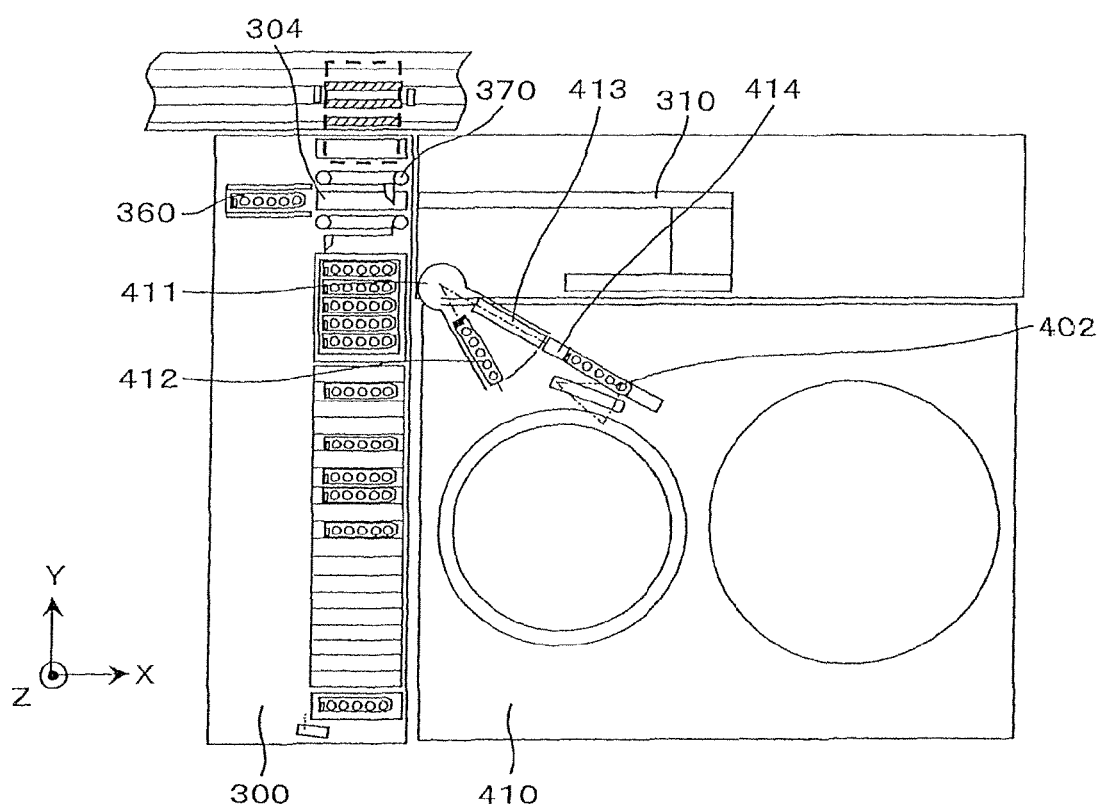
FIG. 12 is a further diagram that illustrates rack transport between the buffer unit and function module in another embodiment of the present invention.
Figure 13:
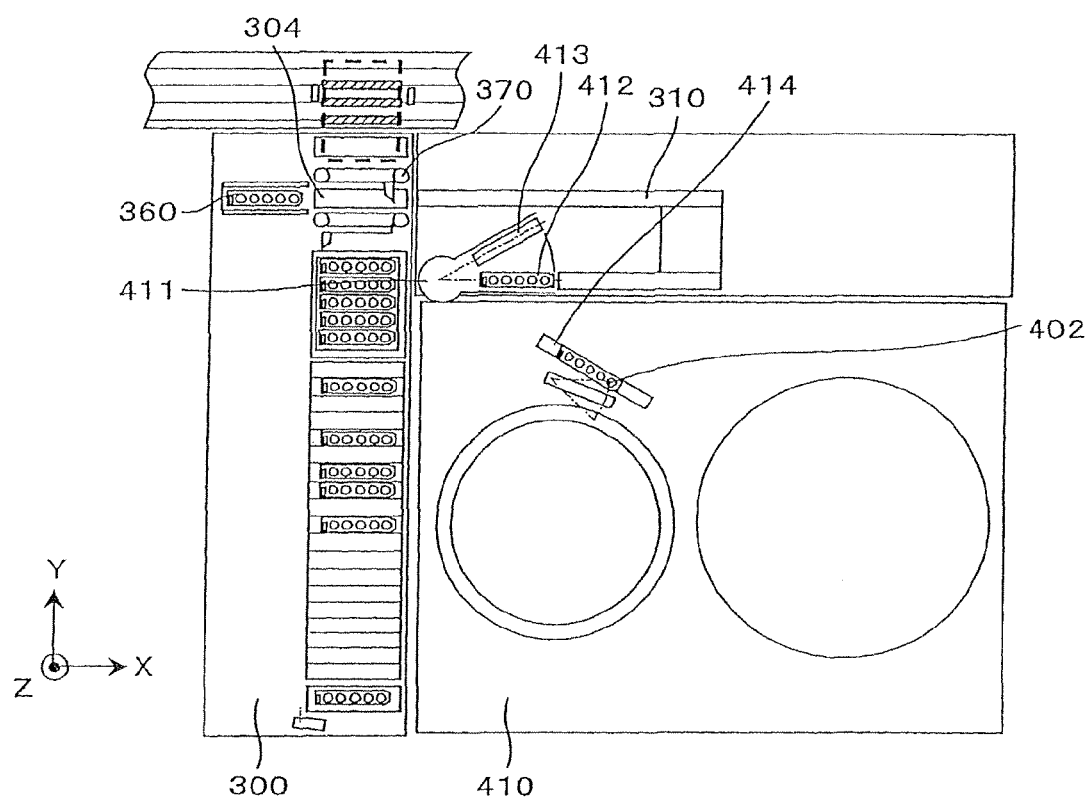
FIG. 13 is a further diagram that illustrates rack transport between the buffer unit and function module in another embodiment of the present invention.

Next, transport of sample racks from the buffer unit 300 to the function module 400 is described below using FIG. 8.

A sample rack to be transported to the function module 400 is moved to the module loading/unloading standby position 304 by the rack-moving mechanism 360 and then moved to the rack transport unit 310 by the rack-unloading mechanism 370.

The rack transport unit 310 is of a mechanical configuration suitable for each function module. The function module 400 of a type which carries a sample rack from the rack transport unit into a function module and after an end of a process such as dispensing, returns the sample rack to the rack transport unit is described below by way of example in the present embodiment. This function module in the embodiment conducts the carrying-in and returning of the rack at independent positions, and has a buffer capable of holding a plurality of racks in series internally.

A sample rack that has been moved to the rack transport unit 310 by the rack-unloading mechanism 370 is further moved to a sample rack loading position 401 in the function module by the rack-moving mechanism.

The sample rack, after being carried into the function module 400 by a rack-loading mechanism (not shown) of the function module, is moved to a processing position 402 and undergoes a dispensing process and/or other necessary processing therein. During this time, if the buffer unit contains a next sample rack to undergo processing in the function module 400, the buffer unit 300 moves the next sample rack to the function module via the rack transport unit in substantially the same sequence as that described above. The function module makes the sample rack stand by in an internal buffer position 403 of the module.

After being processed in the function module 400, the sample rack is returned to a rack-unloading position 404 on the rack transport unit 310 by a rack-unloading mechanism not shown once again. The rack-moving mechanism moves the sample rack in a direction inverse to that of transporting the sample rack to the function module 400, and unloads the sample rack into the module loading/unloading standby position 304 in the buffer unit 300.

Transport of sample racks in another embodiment is described below using FIGS. 9 to 13.

A function module 410 in the another embodiment conducts the carrying-in and returning of a rack from the rack transport unit at the same position and has a fan-shaped buffer 411 capable of holding a plurality of racks circumferentially inside the buffer.

A sample rack that has been moved to the rack transport unit 310 by the rack-unloading mechanism 370 is further moved to a slot 412 in the fan-shaped buffer 411 of the function module by the rack-moving mechanism.

The function module 410 moves the sample rack within the slot 412 to a processing line 414 of the function module 410 by rotating the fan-shaped buffer 411, and performs a necessary process upon the samples. In addition, while the process in the function module 410 is underway, the rack-unloading mechanism 370 moves a next sample rack to be processed in the function module 410, to a slot 413 in the fan-shaped buffer via the rack transport unit 310.

The sample rack that has been processed in the function module 410 is returned from the processing line 414 to the slot 412 in the fan-shaped buffer 411. The function module 410 next rotates the fan-shaped buffer 411 to move the sample rack within the slot 413 to the processing line 414 and perform the necessary process.

The rack held in the slot 412 of the fan-shaped buffer 411 following completion of analysis is returned to the rack transport unit 310 by further rotation of the fan-shaped buffer 411, then moved in a direction inverse to that of transporting the sample rack to the fan-shaped buffer 411, and unloaded into the module loading/unloading standby position 304 in the buffer unit 300. If the function module 410 is to continuously process a further next sample rack, the rack-unloading mechanism 370 moves the next sample rack to be processed in the function module 410, to the slot 412 in the fan-shaped buffer via the rack transport unit 310.

In this way, while the function module 410 is processing a sample rack, another sample rack is always moved to one of the slots in the fan-shaped buffer 411. This enables rack replacement for minimum interruption time in processing with the function module.

Figure 14:
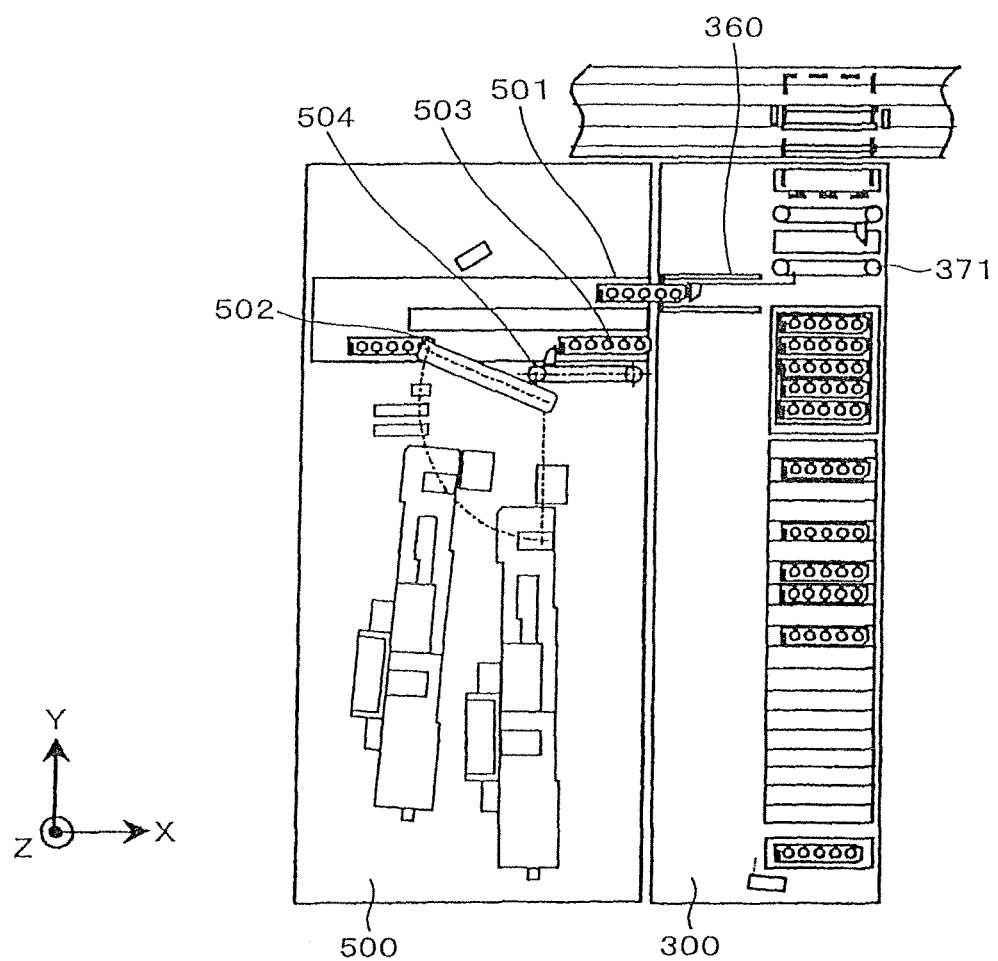
FIG. 14 is a diagram that illustrates rack transport between the buffer unit and an ancillary module.

Next, transport of racks from the buffer unit 300 to the ancillary module 500 is described below using FIG. 14. The ancillary module 500 in the present embodiment is disposed to the left of the buffer unit 300 and has independent positions for sample rack loading and unloading.

The rack-moving mechanism 360 moves a sample rack to be unloaded into the ancillary module 500, to a position in the bucket 361 of the rack-moving mechanism. Next, the rack-moving mechanism 360 moves the bucket 361 to a rack-loading position 501 in the ancillary module 500 by driving the Y-axial driving motor 364. After that, the rack-unloading mechanism 371 unloads the sample rack from the bucket 361 by pushing the rack out into a loading line of the ancillary module.

The sample rack that has been carried into the ancillary module undergoes processing, such as dispensing, in a processing position 502, and then moves to a rack-unloading standby position 503 on an unloading line.

Under a sample rack unloading request from the rack-unloading standby position 503, the rack-moving mechanism 360 of the buffer unit 300 drives the Y-axial driving motor 364 and moves the bucket 361 to the rack-unloading position 503 of the ancillary module. After this, the ancillary module uses a rack-unloading mechanism 504 to move the sample rack to a position in the bucket 361.

Next, transport of the sample rack that has been loaded from the one-rack loader/unloader 320 is described below.

Upon a sample rack being set up on the one-rack loader/unloader 320 by an operator, the rack-moving mechanism 360 drives the Y-axial driving motor 364 to move the bucket 361 to the one-rack loading/unloading position 320. The rack-moving mechanism 360 also drives the X-axial driving motor 365 to move the carriage 363 to the sample rack and then move the carriage upward. After this, the rack-moving mechanism 360 moves the sample rack to the ID reading unit 321, which then reads an ID of the sample rack. Next, the rack-moving mechanism 360 further moves the sample rack to a sample vessel existence detector not shown. This detector confirms whether a sample vessel exists, and reads a sample ID. The kind of process to be performed in the function module is determined from the read rack ID and sample ID information. The sample rack whose sample ID has been read is moved to the bucket 361, next transported to the function module and/or ancillary module in the transport sequence described above, and processed in the module(s). After being processed, the sample rack is likewise unloaded into the one-rack loader/unloader 320 via the bucket 361. This completes the processing sequence.

Provided that a sample rack loader/unloader such as the one-rack loader/unloader 320 shown in the present embodiment is provided in a buffer unit and that a configuration in which electric power, purified water, and other utilities are supplied independently is adopted, processing with a function module is possible, even if the sampler unit 100 or the rack transport line 200 can not operate due to trouble or failure. In addition, a sample rack standing by in the buffer 302 (or the like) of the buffer unit 300 can be unloaded from the one-rack loader/unloader 320 when the operator enters an unloading instruction from a switch or operating unit not shown.

Next, an example of system resetting in the present invention is described below.

As discussed earlier, it is necessary during resetting to clearly determine which sample rack is present in which position. Upon resetting being started, the buffer unit 300 first initializes each mechanism to respective home positions.

Next, the buffer unit 300 moves the bucket 361 of the rack-moving mechanism 360 to a slot position in a buffer, thus moving a sample rack from the slot to the bucket 361.

At this time, if a rack is detected by a in-bucket rack detector 368 provided in the bucket, that is, if a sample rack is present in the slot, the buffer unit moves the bucket 361 to the one-rack loader/unloader 320 first and then the ID reading unit 321, for reading of the sample rack ID. After ID reading, the buffer unit once again returns the bucket to where the rack has existed, and returns the rack to the slot.

If a rack is not detected by the in-bucket rack detector 368 in the bucket, since a rack is absent in the slot, the buffer unit moves the bucket to a next slot and repeats the above sequence.

Information on the existence of a sample rack in each slot, and ID information on all sample racks present in the slots are acquired by the repetition of the sequence.

Next, the buffer unit processes any racks left either on the transport route to the function module 400 within the buffer unit 300, not in the slots, or in the function module 400. The buffer unit processes each of these sample racks in substantially the same way as above. That is, the buffer unit moves the sample rack to the bucket 361 first and then the ID reading unit 321, for reading of the sample rack ID. After reading, the buffer unit stores the rack into an empty slot.

In the above embodiment, although the resetting time can be reduced with a minimum hardware configuration required, since the movement of the sample rack to the bucket is conducted for storage even into an empty slot, a wasteful processing time occurs, for example if no racks exist in the buffers.

Another embodiment for solving this problem is described below.

Figure 15:
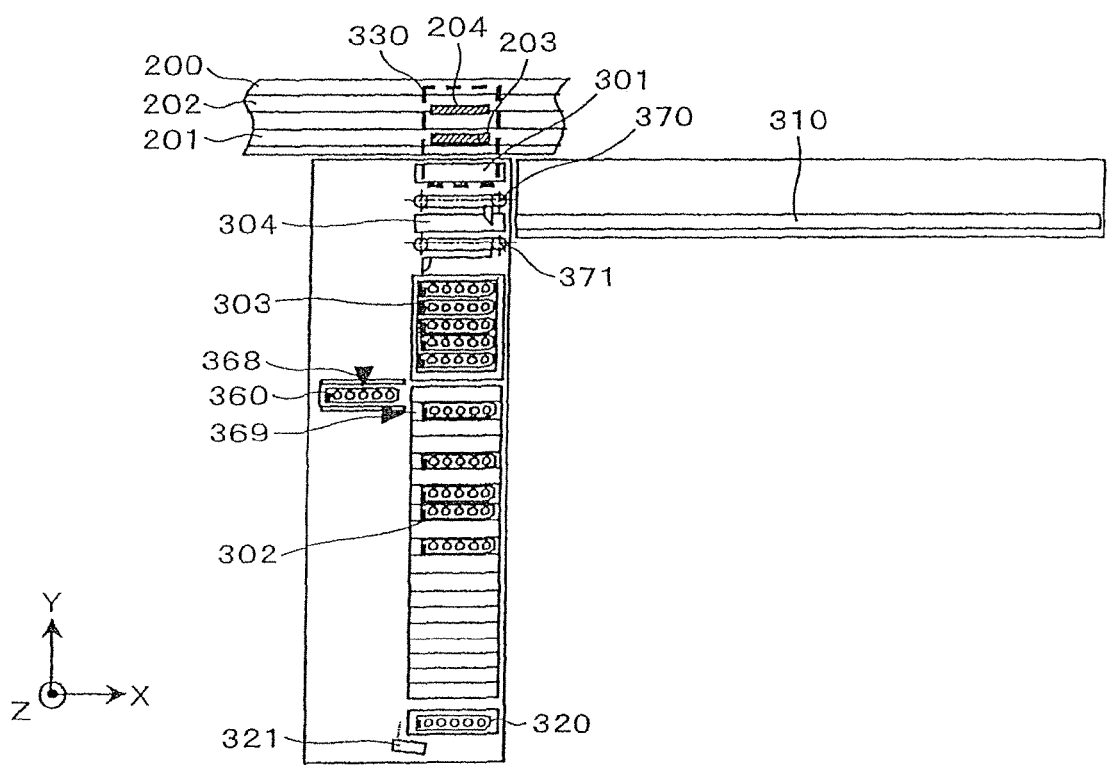
FIG. 15 is a plan view that shows a buffer unit configuration in another embodiment of the present invention.

A buffer unit configuration in the present embodiment is shown in FIG. 15. This configuration differs from that of FIG. 3 in that the bucket itself includes the in-slot rack detector 369 that detects the presence/absence of a rack in each slot.

It is substantially the same in that the buffer unit 300 first initializes each mechanism to the respective home positions and moves the bucket 361 of the rack-moving mechanism 360 to the position of a slot in a buffer. The difference is that the buffer unit next uses the in-slot rack detector 369 within the bucket 361 to detect whether a rack is present in each slot.

The present embodiment is also the same as the embodiment of FIG. 3 in that upon detecting the presence/absence of racks in all slots and moving the bucket 361 to one of the slots in which a rack has existed, the buffer unit moves the rack within this slot to the bucket first and then the ID reading unit 321, and after reading the sample rack ID using the ID reading unit, returns the rack to its original slot.

In addition, the present embodiment is the same as the embodiment of FIG. 3 in that the buffer unit 300 processes any racks left either on the transport route to the function module 400 within the buffer unit, or in the function module 400.

In the present embodiment, efficiency improves since adding the rack detector eliminates the need to operate each mechanism for access to an empty slot. However, even more efficient resetting can be achieved in another embodiment to be described below.

Figure 16:
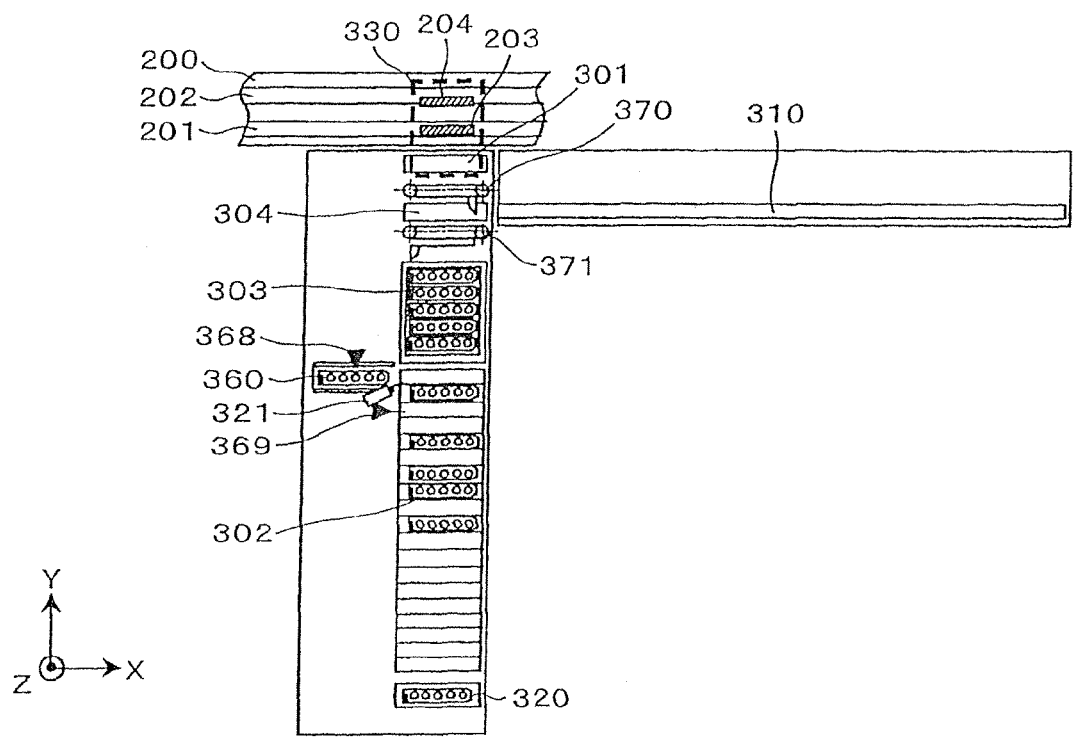
FIG. 16 is a plan view that shows a buffer unit configuration in another embodiment of the present invention.

A buffer unit configuration in the present embodiment is shown in FIG. 16. This configuration differs from that of FIG. 15 in that the bucket has the ID reading unit 321. Minimum pitch A between slots, and mounting pitch B between the in-slot rack detector 369 and the ID reading unit 321 are equal in the present embodiment.

Figure 17:
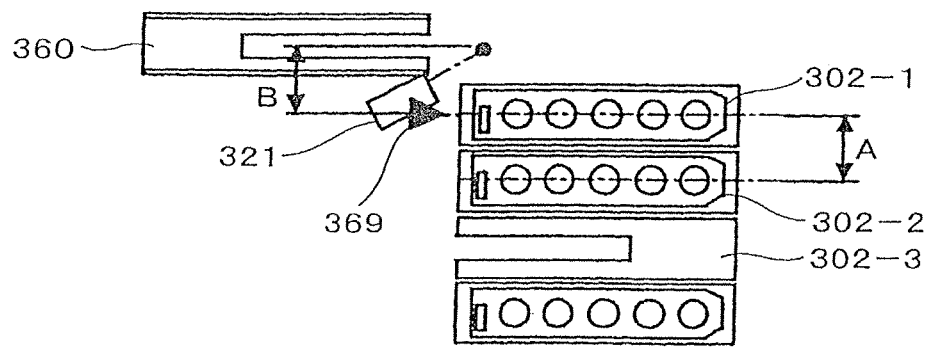
FIG. 17 is a diagram that illustrates in-slot rack detection and rack ID reading.

Resetting in the unit configuration of FIG. 16 is conducted as follows:

The present embodiment is substantially the same as the embodiment of FIG. 15 in that the buffer unit 300 first initializes each mechanism to the respective home positions, next moves the bucket 361 of the rack-moving mechanism 360 to the position of a slot in a buffer, and uses the in-slot rack detector 369 equipped in the bucket 361 to detect whether a rack exists in the slot. FIG. 17 shows a state in which a rack exists in a slot 302-1.

Figure 18:
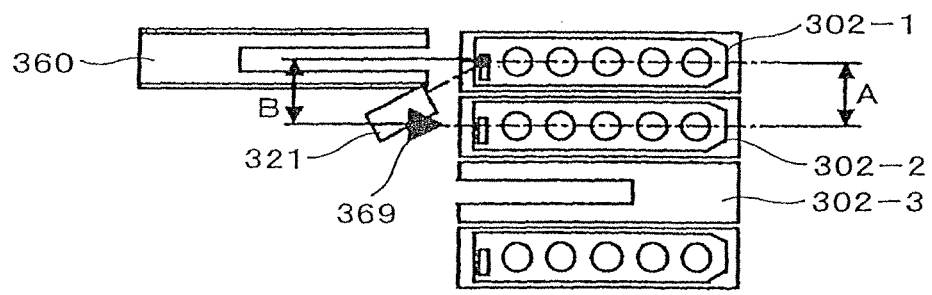
FIG. 18 is another diagram that illustrates in-slot rack detection and rack ID reading.

The buffer unit next moves the bucket 361 through one slot of space. During this movement, if a rack has been detected in the slot 302-1, the ID reading unit 321 reads the sample rack ID. At the same time, whether a rack is present in a slot 302-2 is also detected (see FIG. 18).

If a sample rack is present in the slot 302-2, the buffer unit reads the ID of the rack, and at the same time, detects whether a rack is present in a slot 302-3. In this manner, sample rack ID reading and rack detection are repeated for all slots, and sample rack existence information and sample rack ID information are acquired.

After acquiring the two kinds of information, the buffer unit processes any racks left either on the transport route to the function module 400 within the buffer unit 300, or in the function module 400. The buffer unit stores each of these sample racks into empty slots of the buffers and after moving the bucket 361 through one slot of space, reads the sample rack ID using the ID reading unit 321.

If the mounting pitch B between the in-slot rack detector 369 and the ID reading unit 321 is an integral multiple of the minimum pitch A between slots, efficient operation is implemented since the detection of a sample rack in the slot and the reading of the sample rack ID are simultaneously conducted similarly to the above.

The above four embodiments reduce the processing time in that order. Conversely, however, costs increase for reasons such as there being the need to add hardware, so a scheme appropriate for the resetting capabilities required of the system is desirably selected prior to application.

As described above, all racks that have been loaded from the rack transport unit 200 into the buffer unit 300 are stored into the slots of the buffer 302. Additionally, which rack is stored in which slot is known.

Information on what process the loader 101 is to conduct for each sample, or the sample rack that holds the samples, already exists in a control unit of the system. Furthermore, information on the processing states of each sample in the rack, that is, information on an unmeasured state, a waiting state for measurement results, a measured and waiting state for re-inspection, a measured and waiting state for storage, whether the sample requires processing in other function modules, or the like, is already memorized before resetting is started.

The buffer unit 300, therefore, makes an inquiry to the system control unit as to what process is to be conducted upon the rack present in the buffer unit 300.

The control unit once again determines a transport destination of the rack in accordance with information on reset states of each function module, and then sends an instruction to the buffer unit 300. More specifically, in cases such as there being a function module that has become off-line as a result of unsuccessful recovery from its failure due to resetting, the control unit first determines whether the process that should have originally been conducted in the function module is executable in other function modules. Next if this is possible, the control unit assigns a new transport route to any other appropriate function module, or if the process is inexecutable in other function modules, the control unit sets the transport route leading to the storage unit. In this way, the control unit re-schedules setting of a route different from that which has been determined before apparatus resetting.

In a system configured using a plurality of function modules 400, above processing can be executed completely in parallel between the modules, and the resetting time and a time to a start of re-measurement can be reduced significantly in comparison with the amounts of time required in conventional schemes.

DESCRIPTION OF THE REFERENCE NUMBERS AND SYMBOLS

100 . . . Sampler unit
101 . . . Loader
102 . . . Unloader
103 . . . Load rack moving unit
104 . . . Rack ID reading unit
105 . . . Sample vessel height detection unit
106 . . . Sample ID reading unit
107 . . . Unload rack moving unit
108 . . . Urgent sample loader
109 . . . Loading lever
110 . . . Unloading lever
200 . . . Rack transport unit
201 . . . Supply lane
202 . . . Return lane
203 . . . Supply lane rack loading/unloading position
204 . . . Return lane rack loading/unloading position
300 . . . Buffer unit
301 . . . Rack loading/unloading standby unit
302 . . . Buffer
302-n . . . Buffer slot number
303 . . . Cold storage unit
304 . . . Module loading/unloading standby position
310 . . . Rack transport unit
320 . . . One-rack loader/unloader
321 . . . ID reading unit
330 . . . Rack transfer mechanism
360 . . . Rack-moving mechanism
361 . . . Bucket
362 . . . X-mechanism
363 . . . Carriage
364 . . . Y-axial driving motor
365 . . . X-axial driving motor
366 . . . Z-axial driving motor
367 . . . Slit
368 . . . In-bucket rack detector
369 . . . In-slot rack detector
370, 371 . . . Rack-unloading mechanism
400 . . . Function module
401 . . . Module rack loading position
402 . . . Processing position
403 . . . In-module buffer position
404 . . . Module rack unloading position
410 . . . Function module
411 . . . Fan-shaped buffer
412, 413 . . . Slot in fan-shaped buffer
414 . . . Processing line
500 . . . Ancillary module
501 . . . Ancillary module rack-loading position
502 . . . Ancillary module processing position
503 . . . Ancillary module rack-unloading position
504 . . . Ancillary module rack-unloading mechanism
A . . . Pitch between slots
B . . . Mounting pitch of in-bucket rack detector and in-slot rack detector

The invention claimed is:

1. A sample-processing system comprising:
one or more function modules having different functions and processing capabilities, and
one or more buffer units each combined as a pair with a respective one of the function modules and interconnected via a sample rack transport section that holds a sample vessel and includes a loading unit, transport unit, and storage unit for sample racks each having a specific identification code,
wherein: each of the buffer units undertakes both bi-directional transfer of the sample racks to and from the sample rack transport section, and transport of the sample racks to and from each function module paired with one of the buffer units,
each buffer unit including:
independent slots that each act as a buffer capable of holding a plurality of sample racks;
a sample rack mover that is capable of loading and unloading the sample racks into and from any one of the slots; and
reading means for reading the identification codes assigned to each of the sample racks, and
when the sample-processing system is reset, each buffer unit is configured to:
read the identification code of each sample rack within the buffer unit via the reading means, then determine a transport destination of the sample rack from the read identification code and an operational state of the function module, and restart processing thereof.

2. The sample-processing system according to claim 1, wherein: upon restarting of processing, for each functional module and buffer unit which are combined as a pair, only sample racks other than sample racks existing in the respective buffer unit are stored into an empty slot of the respective buffer unit.

3. The sample-processing system according to claim 1, further comprising:
   detecting means for detecting whether sample racks exist in a slot of the buffer unit.

4. The sample-processing system according to claim 3, wherein: the sample rack mover includes the reading means and the detecting means.

5. The sample-processing system according to claim 4, wherein: the reading means and the detecting means are arranged at a mounting pitch equal to an integral multiple of a minimum pitch between the slots of the buffer.

* * * * *